United States Patent [19]

Roman

[11] 4,218,402
[45] Aug. 19, 1980

[54] PREPARATION OF 2,2-DIMETHYL-3-((OXYIMINO)METHYL)-CYCLOPROPANECARBOXYLIC ACIDS

[75] Inventor: Steven A. Roman, Oakdale, Calif.

[73] Assignee: Shell Oil Company, Houston, Tex.

[21] Appl. No.: 57,632

[22] Filed: Jul. 16, 1979

[51] Int. Cl.² ............................................. C07C 131/02
[52] U.S. Cl. ..................................... 260/546; 560/35; 560/118; 560/124; 562/440; 562/500; 562/506
[58] Field of Search ......................................... 260/546

[56] References Cited

U.S. PATENT DOCUMENTS 4,156,692   5/1979   Roman .................................. 260/546

Primary Examiner—Robert Gerstl

[57] ABSTRACT

2,2-Dimethyl-3-((oxyimino)methyl)cyclopropanecarboxylic acids are prepared by treating the mixed anhydride of acetic and caronaldehydic acids with an acid addition salt of a hydroxylamine or of a hydrocarbyloxylamine followed by hydrolysis of the oxyimino-substituted product thereby obtained.

8 Claims, No Drawings

PREPARATION OF 2,2-DIMETHYL-3-((OXYIMINO)METHYL)CYCLO-PROPANECARBOXYLIC ACIDS

BACKGROUND OF THE INVENTION

1. Field of the Invention

This invention is directed to a new method of preparing 2,2-dimethyl-3-((oxyimino)methyl)cyclopropanecarboxylic acids.

2. Description of the Prior Art

U.S. Pat. No. 3,922,269 discloses the preparation of alkyl esters of 2,2-dimethyl-3-((oxyimino)methyl)-cyclopropanecarboxylic acids by treating an alkyl ester of caronaldehydic acid with an equimolar amount of (an acid addition salt of) hydroxylamine or an alkoxylamine of the formula $R^1ONH_2$ wherein $R^1$ is hydrogen, alkyl or alkenyl in a polar solvent. When it is desired that $R^1$ in the resulting oxime product represent a larger alkyl or alkenyl group than methyl, the patent teaches a two-step process in which one reactant is (an acid addition salt of) hydroxylamine and the resulting oxime is alkylated, as with an alkyl halide in the presence of a hydrogen halide acceptor.

The resulting alkyl esters of 2,2-dimethyl-3-((oxyimino)-methyl)cyclopropanecarboxylic acid are converted under acidic conditions to the free acid and preferably then to the corresponding acid halide for esterification with the desired alcohol or reactive derivative thereof to form the pyrethroid ester pesticides described in the above-noted U.S. patent.

SUMMARY OF THE INVENTION

The present invention is directed to a process for the preparation of 2,2-dimethyl-3-((oxyimino)methyl)cyclopropanecarboxylic acids which comprises treating the mixed anhydride of acetic and caronaldehydic acids with an acid addition salt of hydroxylamine or of a hydrocarbyloxyamine followed by hydrolysis of the oxyimino-substituted product thereby obtained. The process is represented by the following equations:

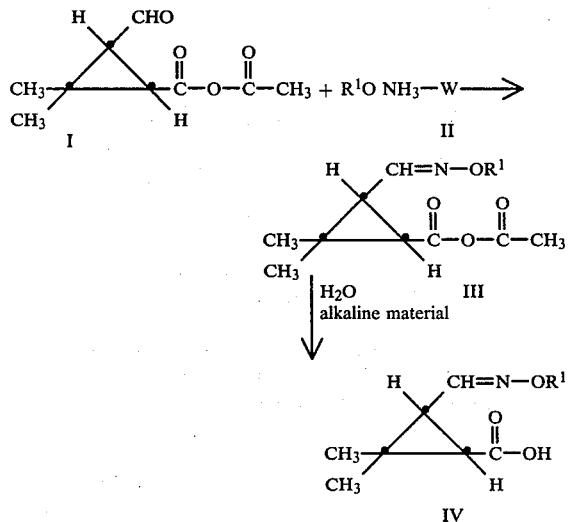

In the above formulas II, III and IV, $R^1$ represents a hydrogen atom; an alkyl group containing from 1 to 10 carbon atoms optionally substituted by one or more halogen atoms; a (cycloalkyl)alkyl group containing from 3 to 7 ring carbon atoms, a total of from 4 to 9 carbon atoms and optionally ring-substituted by one or more halogen atoms; a cycloalkyl group containing from 3 to 7 ring carbon atoms optionally substituted by one or more halogen atoms; an alkenyl group containing 3 to 4 carbon atoms optionally substituted by one or more halogen atoms; an alkynyl group containing from 3 to 4 carbon atoms; or an aryl group containing from 6 to 12 carbon atoms or an aralkyl group containing from 7 to 10 carbon atoms, each optionally substituted by one or more halogen atoms. The halogen atoms are selected from chlorine, bromine and fluorine atoms. In formula II above, W is the anion of a salt forming acid. The anion used to form the acid addition salts of hydroxylamine or of the hydrocarbyloxyamines can be any chemically acceptable anion which will not interfere with the reaction. The anion can be derived from either inorganic or organic acids. Suitable inorganic acids include hydrohalogenic acids such as hydrochloric and hydrobromic; sulfoxy acids such as sulfuric, fluorosulfonic; phosphorus acids such as phosphoric; and nitrogen acids such as nitric acid; or boron acids such as boric or fluoboric acid. Suitable organic acids include lower alkanesulfonic and alkanedioic acids in which the alkane portion contains from 1 to 4 carbon atoms, such as methanesulfonic or oxalic acids. The acid addition salts are preferably prepared from hydrohalogenic acids, e.g., hydrobromic and especially hydrochloric acid.

The present process is useful for the preparation of 2,2-dimethyl-3-((oxyimino)methyl)cyclopropanecarboxylic acids of formula IV

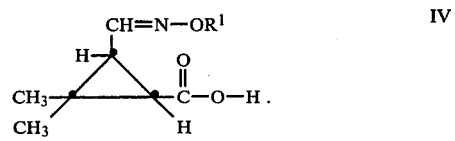

wherein $R^1$ represents a hydrogen atom, an alkyl group containing from 1 to 10 carbon atoms optionally substituted by one or more halogen atoms, a (cycloalkyl)alkyl group containing from 3 to 7 ring carbon atoms, a total of from 4 to 9 carbon atoms and optionally ring-substituted by one or more halogen atoms, a cycloalkyl group containing from 3 to 7 ring carbon atoms optionally substituted by one or more halogen atoms, an alkenyl group containing from 3 to 4 carbon atoms optionally substituted by one or more halogen atoms, an alkynyl group containing from 3 to 4 carbon atoms or an aryl group containing from 6 to 12 carbon atoms or an aralkyl group containing from 7 to 10 carbon atoms, each optionally ring-substituted by one or more halogen atoms.

These acids exhibit geometrical and optical isomerism by virtue of the double bond and the two asymmetric carbon atoms in the molecule. Among the four optical configurations, (1S,tran), (1S,cis), (1R,trans) and (1R,cis), the (1R,cis) is preferred because the pyrethroid esters with the (1R,cis) configuration usually have the highest pesticidal activity although the (1R,trans) esters are also very active.

The first step is conducted in the presence of a solvent. Suitable solvents are non-hydroxylic and unreactive to hydroxylamino, and have some solubilizing properties for salts, e.g., chlorinated hydrocarbons or esters. Suitable chlorinated hydrocarbons contain from 1 to 4 chlorine atoms in combination with an alkane chain containing from 1 to 4 carbon atoms or with a benzene ring, for example, carbon tetrachloride, chloroform, methylene chloride, 1,2-dichloroethane, trichloroethane, perchloroethane, chlorobenzene and 1,2- or 1,3-dichlorobenzene. Methylene chloride is a preferred solvent. Suitable esters are those of lower alcohols and acids each containing from 2 to 6 carbon atoms, for example, ethyl acetate.

The reaction temperature for the first step is not critical and can range from −10° C. to ambient temperatures or slightly above. Generally, the temperature is from about −5° to 40° C. and preferably from about −5° to 5° C.

The molar ratio of the reactants in the first step is not critical and can be widely varied. Generally, a molar ratio of the acid addition salt to the mixed anhydride is from about 1.0 to about 1.6, and preferably from about 1.01 to about 1.4.

Although not required in order for the reaction of the first step to occur, the yield thereof is substantially improved when the reaction takes place in the presence of a water-binding agent which is otherwise inert so as not to react with the compounds involved in the reaction step other than water. The water-binding agent is any anhydrous salt capable of forming a hydrate, suitably an alkali, alkaline earth metal or copper halide or sulfate. Examples of such salts are sodium sulfate, calcium chloride and magnesium sulfate. The water-binding agent is present in a quantity at least sufficient to bind any water present in the reaction mixture and preferably, in a quantity in large excess of that required to bind any water present in the reaction.

The first step is usually conducted by forming a mixture of the mixed anhydride in a solvent and adding the acid addition salt while agitating the reaction mixture, e.g., stirring, and maintaining the desired reaction temperature. The resulting 3-oxyimino-substituted product can be purified or used directly in the hydrolysis step.

The hydrolysis (or second step) is conducted in the presence of an alkaline or acidic material. Any alkaline material can be used to effect hydrolysis but inorganic compounds are very convenient for the purpose. In particular, alkali metal hydroxides, such as sodium hydroxide or potassium hydroxide are used. The alkaline material is added directly to the 3-oxyimino-substituted reaction product in the amount of from about 1 to about 4 moles in excess of the stoichiometric requirement. The hydrolysis step is usually conducted by forming a solution of the 3-oxyimino-substituted mixed anhydride product in a solvent, which is preferably the same as that used in the first step, and adding the alkaline material while agitating, e.g., stirring, and maintaining the desired reaction temperature (which is one within the range specified above for the first step). Ideally, the 3-oxyimino-substituted mixed anhydride need not be separated or purified from the reaction mixture prior to hydrolysis.

The process of the present invention is an improvement over the process taught in U.S. Pat. No. 3,922,269, in that oxyiminomethyl groups other than 3-hydroxyiminomethyl or 3-methoxyiminomethyl are introduced in a one pot reaction, rather than the two-step process of the patent.

The mixed anhydride of acetic and caronaldehydic acids, which is used as a starting material, can be obtained from carene, an inexpensive, readily-available, naturally-occurring terpene found in numerous varieties of pine trees, which can be readily purified by fractional distillation. For example, 2,2-dimethyl-3-(2-oxopropyl)-cyclopropane-1-carboxylic acid can be prepared starting from carene as disclosed in *Agr. Biol. Chem.*, 29, 784 (1965) in which carene was subjected to ozonolysis, the resulting 2,2-dimethyl-3-(2-oxopropyl)-cyclopropane-1-acetaldehyde was treated with sodium acetate in acetic anhydride and fractionally separated under reduced pressure to give the corresponding aldehyde-enol acetate, ozonolysis of this intermediate foflowed by reduction with zinc dust in acetic acid gave 2,2-dimethyl-3-cis-(2-oxopropyl)cyclopropane-1-carboxaldehyde as a product recovered from the neutral portion of the reaction medium and this aldehyde was oxidized with aqueous alkaline potassium permanganate or gaseous oxygen to afford the 2,2-dimethyl-3-(2-oxopropyl)cyclopropane-1-carboxylic acid. This acid, as described in U.S. Pat. No. 4,132,717, is cyclodehydrated to the enol lactone, 4,7,7-trimethyl-3-oxobicyclo[4.1.0]hep-4-en-2-one, which is ozonized and the resulting ozonide subjected to reductive cleavage in the absence of water to yield the mixed anhydride starting reactant of the present process. Preferably, (+)-Δ³-carene is used so that the mixed anhydride starting reactant for the present invention is in the (1R,cis) configuration.

The 3-oxyimino-substituted mixed anhydrides of the formula III

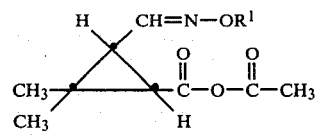

wherein R¹ represents a hydrogen atom, an alkyl group containing from 1 to 10 carbon atoms optionally substituted by one or more halogen atoms, a (cycloalkyl)alkyl group containing from 3 to 7 ring carbon atoms, a total of from 4 to 9 carbon atoms and optionally ring-substituted by one or more halogen atoms, a cycloalkyl group containing from 3 to 7 ring carbon atoms, an alkenyl group containing from 3 to 4 carbon atoms optionally substituted by one or more halogen atoms or alkynyl group containing from 3 to 4 carbon atoms or an aryl group containing from 6 to 12 carbon atoms or an aralkyl group containing from 7 to 10 carbon atoms, each optionally ring-substituted by one or more halogen atoms are novel compounds as well as pyrethroid acid intermediates. These compounds are especially useful when R¹ represents a hydrogen atom, an alkyl group containing from 1 to 6 carbon atoms or a (cycloalkyl)alkyl group containing 3 to 4 ring carbon atoms and a total of 4 to 5 carbon atoms. The resulting pyrethroid esters wherein R¹ is neopentyl, secbutyl or cyclobutylmethyl are particularly useful pesticides, especially when the esters are in the (1R,cis) configuration.

ILLUSTRATIVE EMBODIMENTS

The invention is illustrated by the following embodiments which describe the preparation of typical species of the invention. The embodiments are presented for the purpose of illustration only and should not be regarded as limiting the invention in any way. The identity of the products, including intermediates, was confirmed by elemental, infrared and nuclear magnetic resonance spectral (NMR) analyses as necessary.

EMBODIMENT I (1R,cis)-4,7,7-trimethyl-3-oxabicyclo[4.1.0]hept-4-en-2-one

A solution of 20 g (0.17 mol) of (1R,cis)-2,2-dimethyl-3-(2-oxopropyl)cyclopropane-1-carboxylic acid and 3 g (0.016 mol) of p-toluenesulfonic acid monohydrate in 93 ml of acetic anhydride and 150 ml of benzene was stirred for 30 minutes at 10°–20° C. The slightly darkened mixture was diluted with ether and washed with ice cold saturated sodium bicarbonate solution until the washings were basic. The organic phase was dried over anhydrous magnesium sulfate and decolorized with charcoal. The solvent was evaporated in vacuo to give 24 g (93%) of the product as a tan solid. Recrystallization from pentane gave a white solid mp: 44°–45.5° C., $[\alpha]_D^{25} -85.6°$ (c=2.0; CHCl$_3$).

EMBODIMENT II

Mixed anhydride of acetic and (1R,cis)-caronaldehydic acids

A stream of ozone in air was bubbled into a solution of 18.2 g (0.12 mol) of the product of Embodiment I in 100 ml of methylene chloride at −80° C. until a faint blue color persisted. The solution was purged with air to remove excess ozone and the solvent was evaporated under reduced pressure below 25° C. The residue was dissolved and stirred in 480 ml of ether-acetic acid (2.5 to 1 ratio) in the absence of water and treated portionwise with 43.2 g of zinc dust over 1.5 hours while maintaining the temperature at about 20° C. After stirring for 2 hours, the mixture was filtered to remove zinc salts and the filtrate was evaporated in vacuo. The residue was dissolved in methylene chloride, and dried over anhydrous magnesium sulfate, and the solvent was evaporated to provide, on trituration with a pentane-ether (4:1) mixture, a crude mixture of the mixed anhydride of acetic and (1R,cis)-caronaldehydic acids in 82% yield, as indicated by the presence of strong anhydride bands in the infrared spectrum. The mass spectrometer analysis of this product was identical with the one of the product prepared by acetylation of (1R,cis)-caronaldehydic acid. The NMR spectrum for such an acetylated product was consistent for the mixed anhydride structure and showed the following principal absorptions:

$\delta=1.33$ ppm (singlet) —CH$_3$
$\delta=1.60$ ppm (singlet) —CH$_3$
$\delta=1.9$–2.5 ppm (multiplet) H..Δ..H
$\delta=2.5$ ppm (singlet)

$\delta=9.78$ ppm (doublet) —CHO

EMBODIMENT III

Mixed anhydride of acetic and (1R,cis)-2,2-dimethyl-3-((2,2-dichlorocyclopropylmethoxyimino)methyl)cyclopropane carboxylic acid To a stirred solution containing 0.184 g of the mixed anhydride of acetic and (1R,cis)-caronaldehydic acids, prepared similarly to Embodiment II above, and 0.5 g of sodium sulfate in 10 ml of methylene chloride was added portionwise 0.193 g of 2,2-dichlorocyclopropylmethoxyamine hydrochloride at 0° C. The resulting mixture was stirred at 0° C. for 5 hours, then filtered, and the filtrate was evaporated to yield 0.282 g (88%) of the desired product as an oil.

EMBODIMENT IV (1R,cis)-2,2-dimethyl-3-((2,2-dichlorocyclopropyloxyimino)methyl)cyclopropanecarboxylic acid To a stirred solution of 0.282 g of the mixed anhydride, of Embodiment III above, dissolved in 1 ml H$_2$O and 5 ml tetrahydrofuran, was added several drops of a 10% solution of sodium hydroxide solution to adjust the pH to 7–8. After 10 minutes, the solvent was stripped and the remaining solution was acidified to a pH of 4 and extracted with methylene chloride. The extract was filtered, dried, and stripped to yield 0.150 g of the desired product acid as a thick oil.

EMBODIMENT V

Mixed anhydride of acetic and (1R,cis)-2,2-dimethyl-3-((cyclobutylmethoxyimino)methyl)cyclopropanecarboxylic acid To a stirred solution containing 0.442 g of the mixed anhydride of acetic and (1R,cis)-caronaldehydic acids, prepared similarly to Embodiment II above, and 0.5 g of sodium sulfate in 10 ml methylene chloride, was added portionwise 0.33 g of cyclobutylmethoxyamine hydrochloride at 0° C. The resulting mixture was stirred at 0° C. for 2 days, then filtered, and the filtrate was stripped to yield 0.582 g of the desired product as an oil.

EMBODIMENT VI (1R,cis)-2,2-dimethyl-3-((cyclobutylmethoxyimino)methyl)cyclopropanecarboxylic acid A mixture containing 0.582 g of the mixed anhydride, prepared similarly to Embodiment V above, 2 equivalents of a 10% aqueous sodium hydroxide solution and 4 ml acetone was stirred at room temperature for 15 minutes. The reaction mixture was stripped to remove acetone, acidified to pH 4 with concentrated hydrochloric acid, and extracted with methylene chloride. The extract was dried over anhydrous magnesium sulfate and stripped to yield 0.440 g of an oil. This oil was treated with saturated sodium bicarbonate solution and extracted with ether. The resulting aqueous phase was acidified and extracted with methylene chloride. The extract was dried and stripped to yield 0.351 g (72%) of the desired product.

Following procedures similar to those described in Embodiments III-VI above, the corresponding racemic and (1R,trans) 2,2-dimethyl-3-((2,2-dichlorocyclopropyloxyimino)methyl)cyclopropanecarboxylic acids and 2,2-dimethyl-3-((cyclobutylmethoxyimino)methyl)-cyclopropanecarboxylic acids are prepared as well as 2,2-dimethyl-3-(neopentoxyimino)methyl)-cyclopropanecarboxylic acid, 2,2-dimethyl-3-((sec-butoxyimino)methyl)cyclopropanecarboxylate, and 2,2-dimethyl-3-((cyclopropylmethoxyimino)methylcyclopropanecarboxylate are prepared in their racemic, (1R,trans) and (1R,cis) forms.

I claim:

1. A compound of the formula

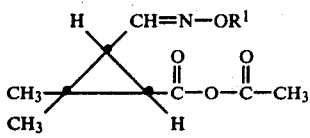

wherein $R^1$ represents an alkyl group containing from 1 to 10 carbon atoms optionally substituted by one or more halogen atoms, a (cycloalkyl)alkyl group containing from 3 to 7 ring carbon atoms, a total of from 4 to 9 carbon atoms and optionally ring-substituted by one or more halogen atoms, a cycloalkyl group containing from 3 to 7 ring carbon atoms, an alkenyl group containing from 3 to 4 carbon atoms optionally substituted by one or more halogen atoms or alkynyl group containing from 3 to 4 carbon atoms or an aryl group containing from 6 to 12 carbon atoms or an aralkyl group containing from 7 to 10 carbon atoms, each optionally ring-substituted by one or more halogen atoms.

2. A compound according to claim 1 wherein $R^1$ is an alkyl group containing from 1 to 6 carbon atoms, or a (cycloalkyl)alkyl group containing 3 to 4 ring carbon atoms and a total of 4 to 5 carbon atoms.

3. A compound according to claim 2 wherein $R^1$ is neopentyl.

4. A compound according to claim 2 wherein $R^1$ is sec-butyl.

5. A compound according to claim 2 wherein $R^1$ is cyclobutylmethyl.

6. A compound according to claim 2 wherein $R^1$ is 2,2-dichloropropylmethyl.

7. A compound according to claim 2 wherein $R^1$ is cyclopropylmethyl.

8. A compound according to claim 1 which is in the (1R,cis) configuration.

* * * * *